US00PP13933P39

(12) United States Plant Patent

Watanabe et al.

(10) Patent No.: US PP13,933 P3

(45) Date of Patent: Jul. 1, 2003

(54) VERBENA PLANT NAMED 'SUNVIVAPA'

(75) Inventors: Yuki Watanabe, Kashiwa (JP); Ryuichi Tachibana, Kawasaki (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/987,811

(22) Filed: Nov. 16, 2001

(65) Prior Publication Data

US 2002/0029397 P1 Mar. 7, 2002

Related U.S. Application Data

(63) Continuation of application No. 09/375,408, filed on Aug. 17, 1999.

(51) Int. Cl.[7] ..... A01H 5/00

(52) U.S. Cl. ..... Plt./308

(58) Field of Search ..... Plt./308

(56) References Cited

U.S. PATENT DOCUMENTS

| | | | | |
|---|---|---|---|---|
| PP8,995 | P | 11/1994 | Tachibana et al. | Plt./308 |
| PP9,014 | P | 12/1994 | Tachibana et al. | Plt./308 |
| PP9,059 | P | 2/1995 | Tachibana et al. | Plt./308 |
| PP9,085 | P | 3/1995 | Tachibana et al. | Plt./308 |
| PP9,121 | P | 4/1995 | Tachibana et al. | Plt./308 |
| PP9,411 | P | 12/1995 | Tachibana et al. | Plt./308 |
| PP10,311 | P | 3/1998 | Tachibana | Plt./308 |
| PP10,705 | P | 11/1998 | Tachibana | Plt./308 |
| PP10,743 | P | 1/1999 | Nagase | Plt./308 |
| PP10,755 | P | 1/1999 | Nagase | Plt./308 |
| PP10,801 | P | 2/1999 | Nagase | Plt./308 |
| PP11,037 | P | 8/1999 | Yomo et al. | Plt./308 |

OTHER PUBLICATIONS

GTITM UPOVROM Citation for 'Sunvivapa' as per JP PBR 8239; Oct. 30, 1995.*

* cited by examiner

*Primary Examiner*—Kent Bell

(74) *Attorney, Agent, or Firm*—Burns, Doane, Swecker & Mathis, L.L.P.

(57) ABSTRACT

Disclosed herein is a Verbena plant which has an erect growth habit and good plant height. The plant abundantly forms flowers in a spike with a great profusion of blooms. The blooming period is late April to November and the flowering duration is long. The whole plant remains in bloom for a considerable period of time. The flower size is large and the petal color is vivid reddish purple without an eye. The plant is highly tolerant to heat and cold, and has high resistance to pests and diseases, particularly powdery mildew, and a high resistance to rain.

2 Drawing Sheets

Botanical/commercial classification: Verbena hybrida× *peruviana*/Verbena plant.

Varietal denomination: cv. 'Sunvivapa'.

BACKGROUND OF THE VARIETY

Verbena is a very popular plant and is used for flower bedding and potting in the summer season. There are only a few varieties of Verbena plants which is much branching, many flowers in a spike, a long flowering duration and which have a high resistance to rain, heat, cold, and disease. Accordingly, this invention was aimed at obtaining a new variety having a erect growth habit, strong branching, many flowers in a spike, long flowering duration, high tolerance to heat and cold, and resistances to diseases and pests, and also having petals that are vivid reddish purple.

The new variety of Verbena plant according to this invention originated from crossing a Verbena hybrida 'Showtime Blaze' (♀) (non-patented in the United States), and a wild type of Verbena plant *Verbena peruviana* 'VBC' (♂) (non-patented in the United States) native to Brazil.

Initially, 45 seedlings were obtained in the autumn of 1992 from crossing of Verbena hybrida 'Showtime Blaze' as female parent and a wild type of Verbena plant 'VBC' (*Verbena peruviana f. rosea*) as pollen parent. From this crossing, 12 seedlings were selected in view of their erect growth habit, branching, and petal color, were propagated by the use of cuttings, and were tested in flower beds and planters from in the spring of 1993 to the autumn of 1994. The botanical characteristics of 12 seedlings were examined and only one seedling was selected, using parent varieties 'Showtime Blaze' and 'VBC' for comparison. As a result, it was concluded that this selected Verbena is distinguishable from any other varieties whose existence is known to us, and is uniform and stable in its characteristics. This new variety of Verbena plant was named 'Sunvivapa'.

In the following description, the color-coding is in accordance with the Horticultural Colour Chart of The Royal Horticultural Society, London, England (R.H.S. Color Chart). A color chart based on The Japan Color Standard for Horticultural Plant (J.H.S. Color Chart) is also added for reference.

The female parent 'Showtime Blaze', used in obtaining this new variety 'Sunvivapa' is commercially available. The main botanical characteristics of 'Showtime Blaze' are as follows:

Plant:

*Growth habit.*—Erect.

*Plant width.*—Medium.

*Plant height.*—High. (25–35 cm)

Stem:

*Diameter.*—Medium.

*Anthocyanin pigmentation.*—Absent.

*Pubescence.*—Present.

*Prickle.*—Absent.
*Branching.*—Medium.
*Subterranean stem.*—Absent.
*Length of internode.*—Medium. (3–4 cm)

Leaf:
*Phyllotaxis.*—Opposite.
*Shape of blade.*—Hastate.
*Blade incision.*—Present.
*Depth of blade incision.*—Shallow.
*Shape of leaf margin.*—Serrated.
*Length.*—Medium.
*Width.*—Medium.
*Color.*—Dark green. (R.H.S. Colour Chart No. 137B, J.H.S. Color Chart No.3508).
*Pubescence.*—Present.
*Petiole.*—Absent.

Flower:
*Shape of cluster.*—Obconical.
*Spike length.*—Medium.
*Spike diameter.*—Medium.
*Facing direction.*—Upward.
*Outward curvature of petal.*—Curved.
*Diameter.*—Large.
*Height.*—Long.
*Color of petal.*—Deep reddish orange (R.H.S. Colour Chart No. 47A, J.H.S. Color Chart No.0708).
*Eye color.*—Absent.
*Varigation.*—Absent.
*Color presentation.*—Substantially even.
*Overlapping of petals.*—Separate.
*Incision of petal.*—Present.
*Number of petals.*—Medium.
*Calyx incision.*—Present.
*Calyx length.*—Long.
*Anthocyanin pigmentation of calyx limb.*—Present.
*Pistil shape.*—Two lobes.
*Stamen number.*—Medium.
*Anther color.*—Yellowish green.
*Peduncle diameter.*—Thin.
*Peduncle length.*—Short.
*Number of flowers.*—Medium.
*Flower fragrance.*—Absent.
*Flowering time.*—Medium.
*Flowering duration.*—Medium.

Physiological and ecological characteristics:
*Tolerance to cold.*—Medium.
*Tolerance to heat.*—Low.
*Resistance to diseases.*—Low.
*Resistance to pests.*—Low.

The pollen parent, a wild type of Verbena plant 'VBC', was used in obtaining this new variety 'Sunvivapa'. The main botanical characteristics of this pollen parent 'VBC' are as follows:

Plant:
*Growth habit.*—Erect.
*Plant width.*—Medium.
*Plant height.*—High.

Stem:
*Diameter.*—Medium. (2–3. mm)
*Anthocyanin pigmentation.*—Present.
*Pubescence.*—Dense.
*Prickle.*—Absent.
*Branching.*—Abundant.
*Subterranean stem.*—Absent.
*Length of internode.*—Medium.

Leaf:
*Phyllotaxis.*—Opposite.
*Shape of blade.*—Hastate.
*Blade incision.*—Present.
*Depth of blade incision.*—Shallow.
*Shape of leaf margin.*—Crenated.
*Length.*—Medium.
*Width.*—Medium.
*Color.*—Dark green. (R.H.S. Colour Chart No. 137B, J.H.S. Color Chart No.3508).
*Pubescence.*—Dense.
*Petiole.*—Absent.

Flower:
*Shape of cluster.*—Turbinate.
*Spike length.*—Medium.
*Spike diameter.*—Medium.
*Facing direction.*—Upward.
*Outward curvature of petal.*—Curved.
*Diameter.*—Medium.
*Height.*—Medium.
*Color of petal.*—Brilliant purple (R.H.S. Colour Chart No. 86D, J.H.S. Color Chart No.8305).
*Eye color.*—Present.
*Size of eye color.*—Medium.
*Varigation.*—Absent.
*Color presentation.*—Substantially even.
*Overlapping of petals.*—Separate.
*Incision of petal.*—Present.
*Number of petals.*—Medium.
*Calyx incision.*—Present.
*Calyx length.*—Medium.
*Anthocyanin pigmentation of calyx limb.*—Present.
*Pistil shape.*—Two lobes.
*Stamen number.*—Medium.
*Anther color.*—Yellowish green.
*Peduncle diameter.*—Medium.
*Peduncle length.*—Medium.
*Number of flowers.*—Medium.
*Flower fragrance.*—Absent.
*Flowering time.*—Very late.
*Flowering duration.*—Long.

Physiological and ecological characteristics:
*Tolerance to cold.*—High.
*Tolerance to heat.*—High.
*Resistance to diseases.*—High.
*Resistance to pests.*—High.

The new variety of Verbena plant 'Sunvivapa' was asexually reproduced by the use of cuttings at the aforementioned Hakushu Nursery Center of SUNTORY Ltd., residing at 2913-1 Torihara, Hakushu-cho, Kitakoma-gun, Yamanashi-ken, Japan, and the homogeneity and stability thereof were confirmed. The instant plant retains its distinctive characteristics and reproduces true to type in successive generations.

SUMMARY OF THE VARIETY

This new variety of Verbena plant has erect growth habit and a tall growth habit. The plant has many branches and abundantly forms flowers in a spike. The blooming period is late April to November and the flowering duration is long. The whole plant remains in bloom for a considerable period of time. The flower petal color is vivid reddish purple color without an eye. The plant is highly tolerant to heat, cold, and has a high resistance to pests and diseases, particularly powdery mildew, and has a high resistance to rain.

The plants described herein were approximately eight months of age and were observed during August while growing in pots. Such plants were being grown at Shimamoto-cho, Mishima-gun, Oosaka-fu, Japan. Approximately ten weeks are required to produce a finished flowering plant following the rooting of cuttings.

DESCRIPTION OF THE VARIETY

Figure 1:
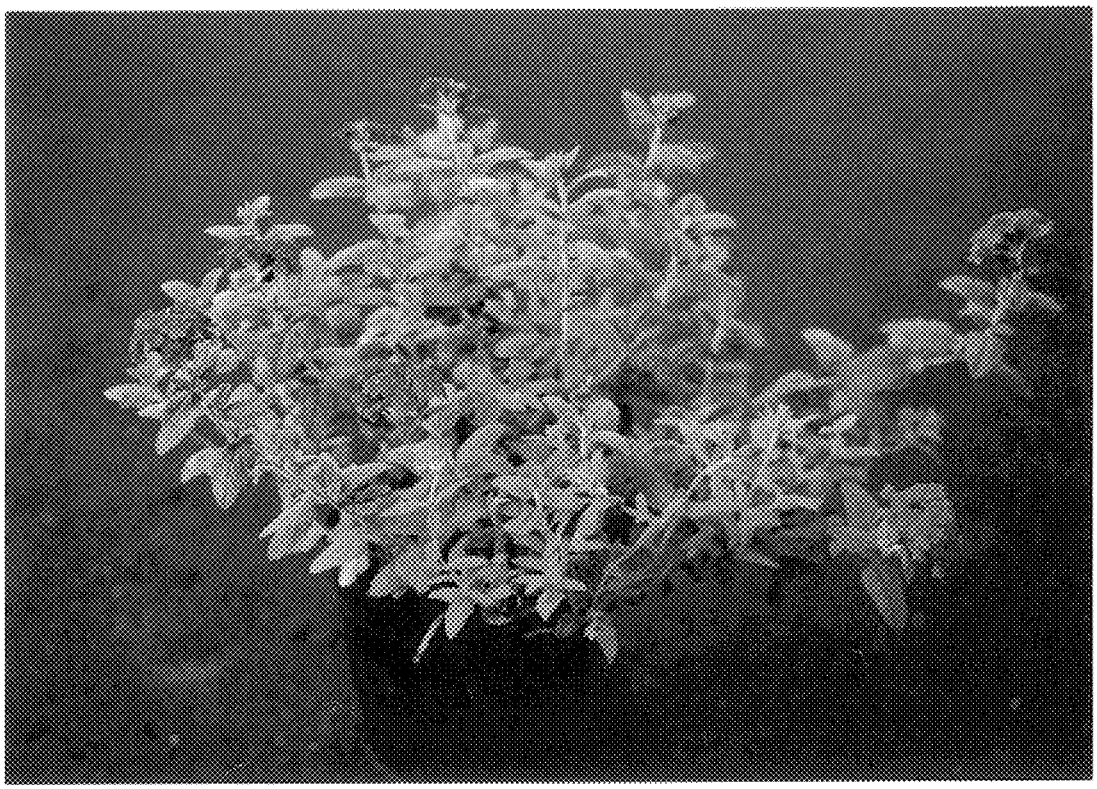
FIG. 1 illustrates a typical plant of the new Verbena variety while growing in a pot.
Figure 2:
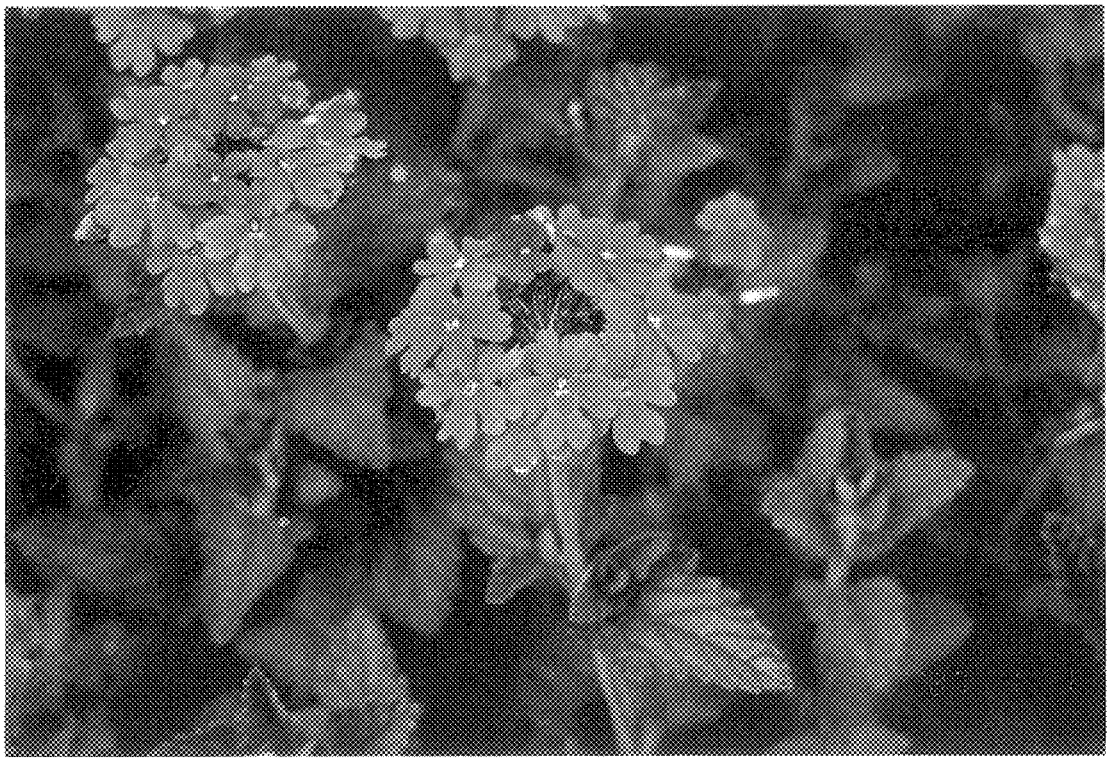
FIG. 2 illustrates a close view of typical foliage and blossoms of the new Verbena variety.

The botanical characteristics of the new and distinct variety of Verbena plant, 'Sunvivapa' are as follows:

Plant:
- *Growth habit.*—Erect.
- *Plant width.*—Approximately 45 cm.
- *Plant height.*—High. (40–50 cm)

Stem:
- *Diameter.*—Medium. (2–3.mm)
- *Length.*—Approximately 40 cm.
- *Color.*—R.H.S. Colour Chart No. 144A.
- *Pubescence.*—Dense.
- *Branching.*—Abundant.
- *Subterranean stem.*—Absent.
- *Length of internode.*—Medium. (4–5 cm)

Leaf:
- *Phyllotaxis.*—Opposite.
- *Shape of blade.*—Hastate.
- *Shape of base.*—Wedge-shaped.
- *Shape of apex.*—Acute.
- *Venation pattern.*—Pinnate.
- *Blade incision.*—Pinatilobed.
- *Depth of blade incision.*—Shallow.
- *Shape of margin.*—Dentate to crenate.
- *Medium.*—(4–5 cm)
- *Width.*—Medium. (3 cm)
- *Color.*—Moderate olive green. (R.H.S. Colour Chart No. 146A, J.H.S. Color Chart No.3509) on the upper surface, and R.H.S. Colour Chart No. 146C on the under surface.
- *Pubescence.*—Moderate in quantity and typical of Verbena.
- *Petiole.*—Present.
- *Petiole diameter.*—Approximately 1.5 mm.
- *Petiole length.*—Approximately 4 mm.
- *Petiole color.*—R.H.S. Colour Chart No. 144A.

Buds:
- *Shape.*—Club-shaped.
- *Length.*—Approximately 1.1 cm.
- *Diameter.*—Approximately 2 mm.
- *Color.*—R.H.S. Colour Chart No. 144A.

Flower:
- *Shape of cluster.*—Funnel-shaped.
- *Spike length.*—Medium. (3 cm).
- *Spike diameter.*—Large. (4–5 cm).
- *Facing direction.*—Upward.
- *Outward curvature of petal.*—Slightly curved.
- *Diameter.*—Large. (20–30 mm)
- *Floral tube.*—Approximately 1.5 cm in length.
- *Petal.*—There is one petal having five lobes per flower. Thus the tubular-shaped flower branches into the five lobes. The apex of each lobe is emarginated, and the texture of the lobe is matt.
- *Color of petal.*—Vivid reddish purple (R.H.S. Colour Chart No.74A, J.H.S. Color Chart No.8907) on the upper surface, and R.H.S. Colour Chart No. 81B to 81D on the under surface.
- *Eye color.*—Absent.
- *Variegation.*—Absent.
- *Color presentation.*—Substantially even.
- *Incision of petal.*—Notched.
- *Calyx.*—The tubular-shaped calyx divides into five sepals. The sepal apex is acuminate and the sepal margin is smooth. The upper and lower surfaces of the sepals are R.H.S. Colour Chart No. 144A. The calyx commonly bears a thin line of R.H.S. Colour Chart No. 61A at the margin. The calyx length is approximately 1 cm and the diameter is approximately 1.8 mm.
- *Pistil number.*—One.
- *Pistil length.*—Approximately 1.5 cm.
- *Stigma.*—Possesses two lobes.
- *Style color.*—R.H.S. Colour Chart No. 144C.
- *Stamen number.*—Commonly Four.
- *Anther color.*—Yellowish green.
- *Peduncle diameter.*—Approximately 1.5 mm.
- *Peduncle length.*—Approximately 2 cm.
- *Peduncle color.*—R.H.S. Colour Chart No. 144A.
- *Number of flowers.*—Commonly approximately 15 per spike.
- *Flower fragrance.*—Absent.
- *Pollen.*—Formed in a sparse quantity, and R.H.S. Colour Chart No. 4B in coloration.
- *Fertility.*—The plant has been sterile during observations to date.
- *Flowering time.*—Late.
- *Flowering duration.*—Long, with an individual bloom commonly lasting approximately 8 to 9 days.

Physiological and ecological characteristics:
- *Tolerance to cold.*—High with the plant having withstood a temperature of −5° C.
- *Tolerance to heat.*—High.
- *Resistance to diseases.*—High, particularly with respect to powdery mildew.
- *Resistance to pests.*—High, particularly with respect to Aphids.

This new variety of Verbena plant is most suitable for flower bedding and potting, particularly in planters, and is further excellent for use as a ground cover.

We claim:

1. A new and distinct variety of verbena plant, substantially as herein illustrated and described, characterized particularly as to novelty by (A) an erect growth habit, (B) a plentiful amount of flowers in a spike with a great profusion of blooms, (C) a long flowering duration, (D) a vivid reddish purple petal color without an eye, and (E) a high resistance to rain, heat, drought, cold diseases and pests.

* * * * *

UNITED STATES PATENT AND TRADEMARK OFFICE

CERTIFICATE OF CORRECTION

PATENT NO. : PP 13,933 P3
DATED : July 1, 2003
INVENTOR(S) : Yuki Watanabe et al.

It is certified that error appears in the above-identified patent and that said Letters Patent is hereby corrected as shown below:

Title page,
Item [73], delete "Assignee: Suntory Limited, Osaka (JP)" and insert
-- [73] Assignee: Suntory Flowers Limited, Tokyo (JP) --.

Signed and Sealed this

Twenty-seventh Day of January, 2004

JON W. DUDAS
*Acting Director of the United States Patent and Trademark Office*